United States Patent [19]
Groth

[11] Patent Number: 5,358,403
[45] Date of Patent: Oct. 25, 1994

[54] GINGIVAL RETRACTION CORD APPLICATOR

[75] Inventor: Eric Groth, Camarillo, Calif.

[73] Assignee: Berport Company, Inc., Camarillo, Calif.

[21] Appl. No.: 157,410

[22] Filed: Nov. 26, 1993

[51] Int. Cl.$^5$ .................................................. A61C 5/14
[52] U.S. Cl. ........................................ 433/136; 433/141
[58] Field of Search .................... 433/136, 138, 141, 3, 433/139; 606/113, 139, 144, 148; 140/118, 119, 120

[56] References Cited

U.S. PATENT DOCUMENTS

| | | | |
|---|---|---|---|
| 3,476,114 | 11/1969 | Shannon et al. | 606/139 |
| 3,596,357 | 8/1971 | Matsumoto | 433/3 |
| 4,396,375 | 8/1983 | Gores | 433/141 |
| 5,281,238 | 1/1994 | Chin et al. | 606/139 |

FOREIGN PATENT DOCUMENTS 2481595  11/1981  France ................................. 433/3

Primary Examiner—Cary E. O'Connor
Attorney, Agent, or Firm—Jack C. Munro

[57] ABSTRACT

A gingival retraction cord applicator comprising a substantially cylindrically shaped handle from which extends at one end thereof a loop of gingival retraction cord which is in the shape of a closed loop. The loop is to be placed around the tooth with the cord twisted by turning of the handle in order to decrease the size of the loop and snugly locate the loop on the tooth with the cord then being physically packed between the gum and the tooth.

3 Claims, 1 Drawing Sheet

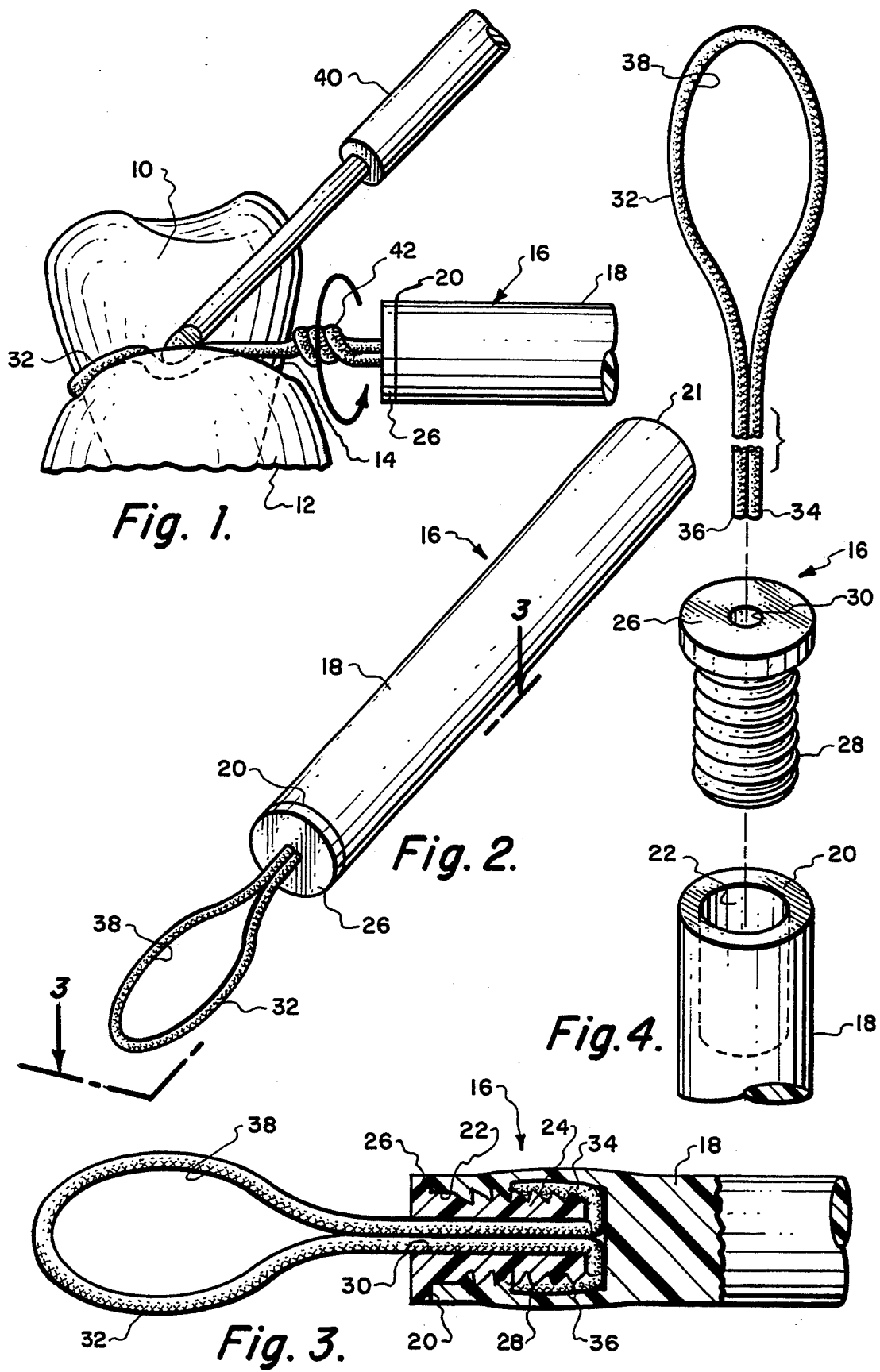

GINGIVAL RETRACTION CORD APPLICATOR

BACKGROUND OF THE INVENTION

1) Field of the Invention

The field of this invention relates to applicators and more particularly to an applicator for gingival retraction cord used by dentists in conjunction with teeth and gums.

2) Description of the Prior Art

Gingival retraction cord has been in long use by dentists. The gingival retraction cord is used by the dentist by being wrapped around a tooth and then packed into the sulcus by the dentist or dental technician. The cord can be unimpregnated and have the purpose of just locating the gum spaced from the tooth permitting the dentist or dental technician access to the tooth located beneath the gum line. The cord can also be impregnated with an astringent, antiseptic, antibiotic, hemostyptic or other type of solution for the purpose of supplying an ingredient to the sulcus. Gingival retraction cord is commonly used by dentists to retract the gum from the tooth so as to facilitate preparation of a tooth for an impression to create a prosthetic.

The typical procedure for supplying gingival retraction cord to the dentist is by a container that contains a given quantity of the cord. The dentist or dental technician is to open the container, pull out a given length of cord and sever the cord with a knife or scissors. The dentist or dental technician then takes the cord and carefully wraps it around the tooth and while holding the ends of the cord with one hand, takes a tool and packs the retraction cord into the sulcus. One problem with this procedure is that it is time consuming. Also, a substantial length of retraction cord is utilized which is greater than what is actually needed, therefore creating waste. There is a need to design an applicator which facilitates the application of the retraction cord and its insertion within the sulcus.

SUMMARY OF THE INVENTION

The primary objective of the present invention is to incorporate a loop of gingival retraction cord in conjunction with a tool with this tool being easily usable to wrap the cord around the tooth facilitating the placement of the gingival retraction cord within the sulcus.

Another objective of the present invention is to construct a tool which is inexpensive to manufacture and therefore can be purchased by a dentist or dental technician at a reasonable price without incurring substantial cost to the patient.

The applicator of the present invention constitutes an elongated cylindrical handle from the end of which extends a loop of gingival retraction cord. The gingival retraction cord could be unimpregnated or could be impregnated prior to its usage. The ends of the gingival retraction cord are conducted through a through hole formed in a plug which is mounted within one end of the handle. The ends of the gingival retraction cord are wedged between the plug and the wall of the recess in the handle. The exterior surface of the plug is hiatused such as including a series of threads or annular ribs which when snugly located within the recess securely clamp the cord against the wall of the recess.

BRIEF DESCRIPTION OF THE DRAWING

FIG. 1 is a view depicting usage of the applicator of the present invention in conjunction with a tooth showing packing of the gingival retraction cord within the sulcus;

FIG. 2 is an isometric view of the applicator of the present invention;

FIG. 3 is a longitudinal cross-sectional view through a portion of the applicator of the present invention taken along line 3—3 of FIG. 2; and FIG. 4 is an exploded isometric view of the components that make up the construction of the applicator of the present invention.

DETAILED DESCRIPTION OF THE SHOWN EMBODIMENT

Referring particularly to the drawing, there is depicted a tooth 10 being mounted within gum 12, with it being understood that normally there will be plurality of teeth 10 within the mouth of the human. The tooth 10 protrudes above the gum line 14 of the gum 12. Between the gum line 14 and the tooth 10 there is located the sulcus, with this portion of the gum 12 being expandable to move away from the tooth 10.

The applicator 16 of this invention comprises a cylindrically shaped elongated handle 18 which normally will be constructed of a plastic material with generally Delrine ® being preferred. The handle 18 has a front end 20 and a rear end 21. Within the front end 20 there is formed an open-ended enlarged recess 22. Snugly mountable within the recess 22 is the body 24 of a plug 26. The exterior surface of the body 24 is hiatused being formed into a series of annular ribs 28. Other forms of hiatuses could be utilized such as threads or the like. It is the function of the ribs 28 to form a tight connection between the plug 26 and the handle 18 preventing withdrawal of the plug 26 from the handle 18.

The plug 26 also includes a centrally located through opening 30. A length of gingival retraction cord 32 is selected which terminates in ends 34 and 36. The ends 34 and 36 are conducted through the through opening 30 with ends 34 and 36 then being located against the ribs 28. The body 24 is then press fitted into the enlarged recess 22 which results in a wedging action occurring of the ends 34 and 36 between the body 24 and the handle 18. This will now prevent accidental withdrawing of the gingival retraction cord 34 from the handle 18 during usage of the applicator 16.

The retraction cord 32 forms a closed loop 38. The tube 10 is to be located within the loop 38 with the cord 32 located in contact with the gum line 14. The dentist or dental technician is to then twist the handle 18 forming a twisted area 42 within the gingival retraction cord 32. This twisting is to occur until the cord 32 is snugly mounted around the tooth 10. Some teeth are larger than others while other teeth, of course, are quite small in size. The twisted area 42 is to take up the slack of the cord 32 and snugly locate the cord 32 about the tooth 10. The dentist or dental technician then takes a separate implement 40 to pack the cord 32 within the sulcus as is depicted within FIG. 1.

When the cord 32 is completely packed within the sulcus, the dentist or dental technician can then merely release the handle 18 with the applicator 16 assuming a hanging position. Normally, this hanging position will occur for a certain period of time such as five minutes to a half hour which is sufficient time to permit any impregnated solution within the cord 32 to perform its desired function in the area of the sulcus. When it is desired to remove the cord 32, easy removal is accomplished by merely grasping of the handle 18 and disengaging of the cord 32 from the tooth 10. If the dentist or dental technician desires, the cord 32 can be severed in the area of the twisted section 42 with the handle 18 then being discarded. When it is desired to remove to cord 32, the dentist or dental technician will take a pair of tweezers and clamp onto the cord 32 and disengage such from the tooth 10.

What is claimed is:

1. A gingival retraction cord applicator comprising:
   a handle;
   a loop of gingival retraction cord terminating in a pair of ends, said ends being permanently secured to said handle, a portion of said ends abutting making said loop closed; and
   whereby said loop is to be placed around a tooth with the cord located against the gum and then the cord is tightened on the tooth by turning of the handle which twists the cord decreasing the size of the loop with the cord being then being packed between the gum and the tooth.

2. The gingival retraction cord applicator as defined in claim 1 wherein:
   said handle being substantially cylindrical in configuration defining a front end wall, said pair of ends of said loop being secured to said front end wall.

3. A gingival retraction cord applicator comprising:
   a handle;
   a loop of gingival retraction cord terminating in a pair of ends, said ends being secured to said handle, a portion of said ends abutting making said loop closed; and
   whereby said loop is to be placed around a tooth with the cord located against the gum and then the cord is tightened on the tooth by turning of the handle which twists the cord decreasing the size of the loop with the cord being then being packed between the gum and the tooth;
   said handle being substantially cylindrical in configuration defining a front end wall, said pair of ends of said loop being secured to said front end wall; and
   a plug being fixedly mounted in said front end wall of said handle, said front end wall of said handle having an enlarged recess, said enlarged recess having a wall surface, said plug having a body to be located within said enlarged recess in a snug fitting manner, the exterior surface of said body including a hiatused section, said plug having a through opening, said pair of ends of said loop to be conducted through said through opening with said pair of ends being clamped between said hiatused section and said wall surface of said enlarged recess.

* * * * *